(12) United States Patent
Wang

(10) Patent No.: US 7,645,578 B2
(45) Date of Patent: *Jan. 12, 2010

(54) CLEAVAGE OF RNA AT REDUNDANT SITES

(75) Inventor: Hui Wang, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/591,260

(22) Filed: Oct. 31, 2006

(65) Prior Publication Data

US 2008/0124713 A1 May 29, 2008

(51) Int. Cl.
*C12Q 1/68* (2006.01)
*C07K 14/00* (2006.01)

(52) U.S. Cl. .......................................... 435/6; 530/350

(58) Field of Classification Search .................. 435/6; 536/22.1; 530/350
See application file for complete search history.

(56) References Cited

U.S. PATENT DOCUMENTS

| | | | | | |
|---|---|---|---|---|---|
| 5,268,289 | A | * | 12/1993 | Dahl et al. | 435/199 |
| 5,635,377 | A | * | 6/1997 | Pederson et al. | 435/91.3 |
| 5,849,900 | A | * | 12/1998 | Moelling | 536/24.5 |
| 6,004,755 | A | * | 12/1999 | Wang | 435/6 |
| 6,613,516 | B1 | | 9/2003 | Christians et al. | |
| 7,022,832 | B2 | * | 4/2006 | Malvy et al. | 536/24.5 |
| 2005/0164226 | A1 | * | 7/2005 | Huang | 435/6 |
| 2006/0211024 | A1 | | 9/2006 | Corn et al. | |
| 2007/0009913 | A1 | * | 1/2007 | Wang | 435/6 |
| 2007/0009915 | A1 | * | 1/2007 | Wang | 435/6 |
| 2008/0102454 | A1 | * | 5/2008 | Wang | 435/6 |

FOREIGN PATENT DOCUMENTS

| | | |
|---|---|---|
| WO | WO 9808977 | 3/1998 |
| WO | WO 9808977 A1 * | 3/1998 |
| WO | WO 0053745 A1 * | 9/2000 |
| WO | WO2005098029 A2 | 10/2005 |

OTHER PUBLICATIONS

Hoshika, S. et al. Nucleosides and nuceotides. Part 226: Alternate-strand triple-helix formation by 3'-3'-linked oligodeoxynucleotides composed of asymmetrical sequences. Bioorganic & Medicinal Chemistry Letters, vol. 14, pp. 3333-3336, 2004.*

GB Search Report, Application No. GB0720572.7, mailed Feb. 20, 2008, 1 page, corresponding to U.S. Appl. No. 11/591,260.

* cited by examiner

*Primary Examiner*—Suryaprabha Chunduru

(57) ABSTRACT

The invention relates to methods for treating samples of RNA. In an embodiment the method includes contacting the sample of RNA with a set of oligodeoxynucleotides to provide a DNA/RNA duplex. The method includes contacting the DNA/RNA duplex with an enzyme having a DNA:RNA nuclease activity to provide a digested RNA sample. Kits in accordance with the invention are also described.

21 Claims, 1 Drawing Sheet

CLEAVAGE OF RNA AT REDUNDANT SITES

FIELD OF THE INVENTION

The invention relates generally to methods of biochemical analysis. More specifically, the invention relates to a method of treating a sample of RNA to enhance analysis of the sample.

BACKGROUND OF THE INVENTION

There has been great interest in the analysis of small RNAs, such as short interfering RNAs (siRNAs), microRNAs (miRNA), tiny non-codingRNAs (tncRNA) and small modulatory RNA (smRNA), since the discovery of siRNA biological activity over a decade ago. See Novina et al., Nature 430:161-164 (2004). Even though the functions of most discovered miRNAs remain a mystery, it has become clear that they exist in abundance in plants and animals, with up to tens of thousands of copies per cell. In the fruit fly, 78 have been identified, and over 300 have been identified in human (see the public database accessible via the website located by placing "www" in front of ".sanger.ac.uk/cgi-bin/Rfam/mirna/browse.pl"). The levels of individual miRNAs seem to vary with developmental stages and tissue types. The level of fluctuation may be correlated with phenotype, mRNA levels, or protein levels for better biological insight. Thus quantitative measurements of miRNA may be of great importance. Further, viral miRNAs have been identified and may play a role in latency (see Pfeffer et al., Science, 304: 734-736 (2004)), making the detection and quantification of miRNAs a potentially valuable diagnostic tool.

Straightforward and reliable methods for simultaneously analyzing several constituents of a complex RNA sample are extremely desirable. While current methods of preparing RNA samples are quite useful, there is a continuing need for methods of preparing RNA samples for analysis or for other purposes.

SUMMARY OF THE INVENTION

The invention thus relates to novel methods for treating RNA samples. In one embodiment of the present invention, a method of treating a sample of RNA is provided wherein the method includes: obtaining a set of Oligodeoxynucleotides, the set of Oligodeoxynucleotides comprising member Oligodeoxynucleotides. Each member Oligodeoxynucleotide is directed to a redundant RNA cleavage site. The sample of RNA is contacted with the set of Oligodeoxynucleotides under stringent assay conditions to provide DNA/RNA duplexes, and the DNA/RNA duplexes are contacted with an enzyme having a DNA:RNA nuclease activity to provide a digested RNA sample.

Kits in accordance with the invention are also described, wherein the kits include a set of oligodeoxynucleotides and an enzyme having a DNA:RNA nuclease activity.

Additional objects, advantages, and novel features of this invention are set forth in part in the description follows and in part will become apparent to those skilled in the art upon examination of the following specifications or may be learned by the practice of the invention. The objects and advantages of the invention may be realized and attained by means of the instruments, combinations, compositions and methods particularly pointed out herein and in the appended claims.

BRIEF DESCRIPTION OF THE DRAWINGS

These and other features of the invention will be understood from the description of representative embodiments of the method herein and the disclosure of illustrative apparatus for carrying out the method, taken together with the FIGURE, wherein.

Figure 1:
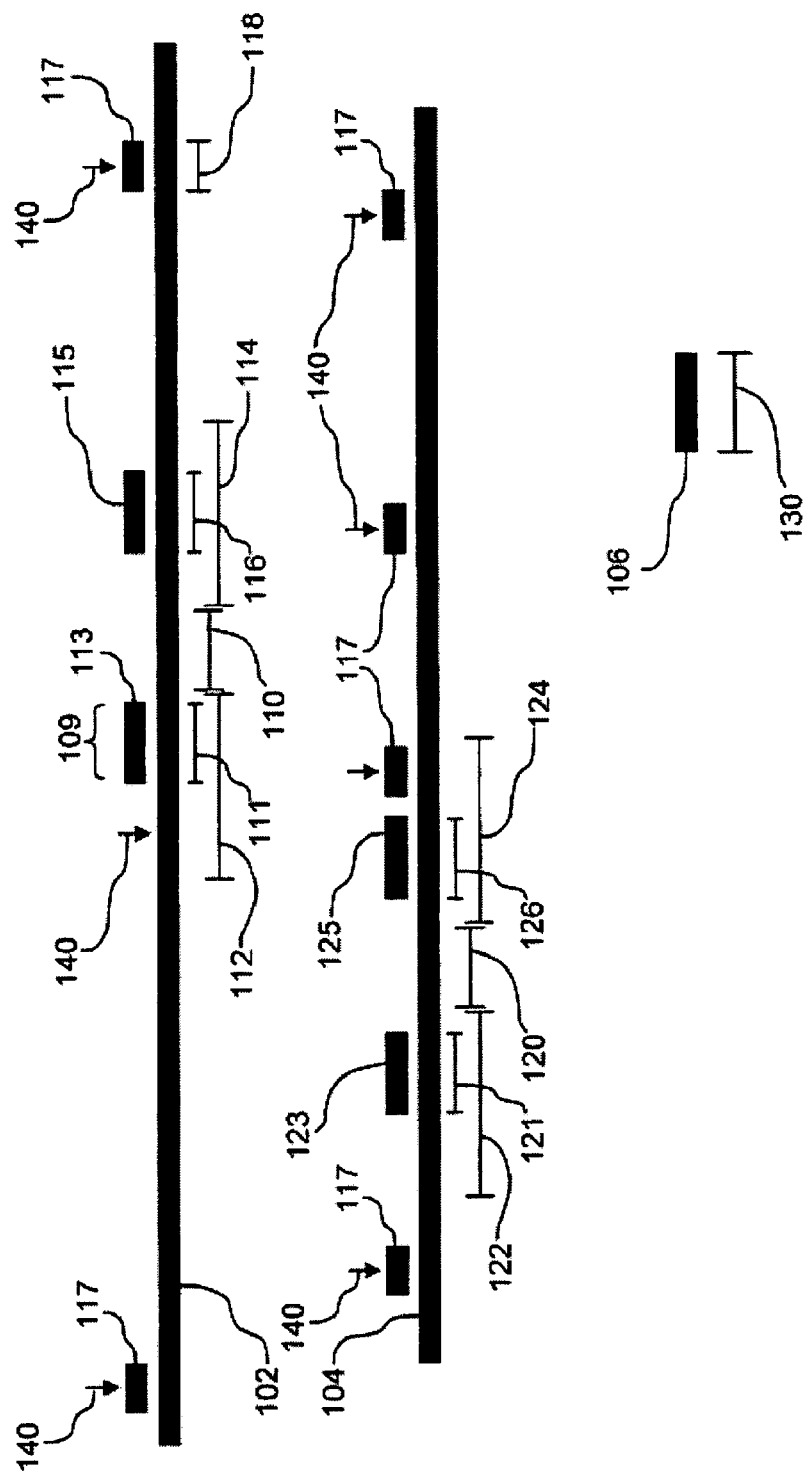
FIG. 1 illustrates several RNA and oligodeoxynucleotide molecules, and various features and relationships between the features are shown.

The components of FIG. 1 are broadly illustrative and are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an oligodeoxynucleotide" includes a plurality of oligodeoxynucleotides. Similarly, reference to "an RNA" includes a plurality of different identity (sequence) RNA species.

Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. In this specification and in the claims that follow, reference will be made to a number of terms that shall be defined to have the following meanings unless a contrary intention is apparent.

"Optional" or "optionally" means that the subsequently described circumstance may or may not occur, so that the description includes instances where the circumstance occurs and instances where it does not. For example, if a step of a process is optional, it means that the step may or may not be performed, and, thus, the description includes embodiments wherein the step is performed and embodiments wherein the step is not performed (i.e. it is omitted).

An "oligonucleotide" is a molecule containing from 2 to about 100 nucleotide subunits. An "oligodeoxynucleotide" is a molecule containing from 2 to about 100 deoxyribonucleotide subunits. The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner similar to that of two naturally occurring nucleic acids, e.g., can participate in Watson-Crick base pairing interactions. The terms "nucleoside", "nucleotide", "oligodeoxynucleotide", and "deoxyribonucleotides" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Modified nucleosides or nucleotides also include molecules having structural features that are recognized in the literature as being mimetics, derivatives, having similar properties, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking moieties.

A duplex is a double stranded structure typically formed between complementary nucleic acid sequences. A DNA/RNA duplex is a double stranded structure formed between a DNA molecule and an RNA molecule. Similarly, an RNA/RNA duplex is a double stranded structure formed between an RNA molecule and another RNA molecule (or different portions of the same RNA molecule).

"Sequence" may refer to a particular sequence of bases and/or may also refer to a polynucleotide having the particular sequence of bases. Thus a sequence may be information or may refer to a molecular entity, as indicated by the context of the usage.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A moiety is generally bound to one or more other moieties to provide a molecular entity. As a simple example, a hydroxyl moiety bound to an ethyl moiety provides an ethanol molecule. At various points herein, the text may refer to a moiety by the name of the most closely related structure (e.g. an oligonucleotide moiety may be referenced as an oligonucleotide, a mononucleotide moiety may be referenced as a mononucleotide). However, despite this seeming informality of terminology, the appropriate meaning will be clear to those of ordinary skill in the art given the context, e.g. if the referenced term has a portion of its structure replaced with another group, then the referenced term is usually understood to be the moiety. For example, a mononucleotide moiety is a single nucleotide which has a portion of its structure (e.g. a hydrogen atom, hydroxyl group, or other group) replaced by a different moiety (e.g. a linking group, an observable label moiety, or other group). Similarly, an oligonucleotide moiety is an oligonucleotide which has a portion of its structure (e.g. a hydrogen atom, hydroxyl group, or other group) replaced by a different moiety (e.g. a linking group, an observable label moiety, or other group). "Nucleotide moiety" is generic to both mononucleotide moiety and oligonucleotide moiety.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 2%, at least about 5%, at least about 10%, at least about 20%, at least about 30%, at least about 50%, at least about 80%, or at least about 90% of the sample (excluding solvents). For example, a sample of isolated RNA will typically comprise at least about 2% total RNA, or at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, affinity chromatography, and sedimentation according to density. In typical embodiments, the sample or the enzyme having a DNA:RNA nuclease activity is in isolated form; more typically, both are obtained in isolated form prior to use in the present methods.

The term "sample" as used herein relates to a material or mixture of materials, typically, although not necessarily, in fluid form, containing one or more components of interest.

The term "analyte" is used herein to refer to a known or unknown component of a sample. In certain embodiments of the invention, an analyte may specifically bind to a capture agent on a support surface if the analyte and the capture agent are members of a specific binding pair. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). A "target" references an analyte.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

The terms "specific binding", "specifically bind", or other like terms, refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the binding constant of a capture agent and analyte is greater than $10^6$ $M^{-1}$, greater than $10^7$ $M^{-1}$, greater than $10^8$ $M^{-1}$, greater than $10^9$ $M^{-1}$, greater than $10^{10}$ $M^{-1}$, usually up to about $10^{12}$ $M^{-1}$, or even up to about $10^{15}$ $M^{-1}$.

The term "stringent assay conditions" as used herein refers to conditions that are compatible to produce binding pairs of nucleic acids, e.g., capture agents and analytes, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions. The desired level of specificity in the assay typically provides for sequence-specific binding to occur between complementary sequences of nucleic acids.

A "stringent hybridization" and "stringent hybridization wash conditions" in the context of nucleic acid hybridization (e.g., as in Southern or Northern hybridizations, or hybridization of molecules in solution) are sequence dependent, and are different under different experimental conditions. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1× SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acids are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are oligodeoxynucleotides (e.g. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., a known analyte that is of interest, is used synonymously with the term "pre-determined analyte".

The term "array" encompasses the term "microarray" and refers to an ordered array of capture agents for binding to aqueous analytes and the like. An "array" includes any two-dimensional or substantially two-dimensional (as well as a three-dimensional) arrangement of spatially addressable regions (i.e., "features") containing capture agents, particularly polynucleotides, and the like. Any given support may carry one, two, four or more arrays disposed on a surface of a support. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 100 $cm^2$, 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of the same or different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Arrays can be fabricated by depositing (e.g., by contact- or jet-based methods) either precursor units (such as nucleotide or amino acid monomers) or pre-synthesized capture agent. An array is "addressable" when it has multiple regions of different moieties (e.g., different capture agent) such that a region (i.e., a "feature" or "spot" of the array) at a particular predetermined location (i.e., an "address") on the array will detect a particular sequence. An "array layout" refers to one or more characteristics of the features, such as feature positioning on the support, one or more feature dimensions, and an indication of a moiety at a given location. "Interrogating" the array refers to obtaining information from the array, especially information about analytes binding to the array. "Hybridization assay" references a process of contacting an array with a mobile phase containing analyte. An "array support" refers to an article that supports an addressable collection of capture agents.

Small RNA references RNAs less than about 500 bases long, e.g. less than about 400 bases long, less than about 300 bases long, less than about 200 bases long, less than about 100 bases long, less than about 60 bases long, less than about 50 bases long, less than about 40 bases long, or less than about 35 bases long. In particular embodiments, the small RNA may be selected from short interfering RNAs (siRNAs), microRNAs (miRNA), tiny non-coding RNAs (tncRNA) and small modulatory RNA (smRNA), or combinations thereof. See Novina et al., Nature 430: 161-164 (2004). In particular embodiments, small RNAs may be at least about 4 bases long, at least about 6 bases long, at least about 8 bases long, or longer.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. "Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region may be paired with its complementary base, i.e. following normal base-pairing rules. "Substantial sequence complementarity" permits one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The complementary region is the region that is complementary between a first polynucleotide and a second polynucleotide (e.g. a target analyte and a capture agent; further e.g. an RNA cleavage site and an oligodeoxynucleotide that is complementary to that RNA cleavage site). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long. In various typical embodiments, the complementary region may be up to about 200 bases long, or up to about 120 bases long, up to about 100 bases long, up to about 80 bases long, up to about 60 bases long, up to about 45 bases long, or up to about 40 bases long.

Sequence complementarity between two nucleic acid molecules may expressed in terms of a percentage calculated as follows: When a corresponding position in a complementary sequence relative to a reference sequence is occupied by a complementary base (e.g. a base that would be expected to base pair with the base in the reference sequence), then the sequences are complementary at that position. The percent of sequence complementarity can be maximized by aligning the compared sequences alongside each other, sliding them back and forth relative to each other, and conservatively introducing gaps in the sequences where necessary. The percent of sequence complementarity is calculated by counting the number of complementary aligning residues dividing by the total length of the aligned region, including gaps in both sequences, and multiplying by 100. Sequence complementarity would thus be expressed as, e.g., "60% complementary over 40 bases," or "57% identity over 30 amino acids." In the example indicated below, the compared sequence ("Comp": (SEQ ID NO:1) sequence is 80% complementary over 44 bases compared to the reference ("Ref": (SEQ ID NO:2) sequence ((35 complementary bases/44 bases)×100%), where 44 is the total length of the aligned region, including gaps in both sequences.

```
Comp    UAUCCUCCAGUAACAUGUAAUGACGAAUGGAGGGUC-UUCUAAU    (SEQ ID NO: 1)  44 bases
        |||  |||||||||| ||||||||||||| |||||  |   |||                    35 compltry
Ref     AUA--AGGUCAUUGU--AUUACUGCUUACGACCCAGUAUAGUUA    (SEQ ID NO: 2)  44 bases
```

Note that the same sequences below (SEQ ID NO:1 and SEQ ID NO:2) may also be used to show that the compared sequence is 90% complementary over 31 bases compared to the reference sequence ((28 complementary bases/31 bases)× 100%), where 31 is the total length of the aligned region, including gaps in both sequences.

```
Comp    UAUCCUCCAGUAACAUGUAAUGACGAAUGGAGGGUC-UUCUAAU    (SEQ ID NO: 1)  31 bases
             ||||||||| |||||||||||||| |||||                             28 compltry
Ref          AUA--AGGUCAUUGU--AUUACUGCUUACGACCCAGUAUAGUUA (SEQ ID NO: 2)  31 bases
```

"Upstream" as used herein refers to the 5' direction along a polynucleotide, e.g. an RNA molecule. "Downstream" refers to the 3' direction along the polynucleotide. Hence, an "upstream proximal region" is located in the 5' direction from the respective target site. Similarly, a "downstream proximal region" is located in the 3' direction from the respective target site. "3'-" and "5'-" have their conventional meaning as known in the art. If the polynucleotide is double stranded, one of the strands is selected as the reference strand, e.g. the strand that is labeled, or the strand that is not labeled (or some other criteria or feature of the strand may be used to designate one strand as the reference strand).

If a first polynucleotide, e.g. an oligodeoxynucleotide, is "directed to" a second polynucleotide, e.g. a RNA molecule, the first polynucleotide has a sequence that is complementary to a sequence in that second polynucleotide and will specifically bind (i.e. hybridize) to that second polynucleotide under hybridization conditions. The hybridization conditions typically are selected to produce binding pairs of polynucleotides, e.g. DNA/RNA duplexes, of sufficient complementarity to provide for the desired level of specificity while being incompatible to the formation of binding pairs between binding members of insufficient complementarity to provide for the desired specificity. Such hybridization conditions are typically known in the art.

Referring to the FIGURE, several RNA and Oligodeoxynucleotide molecules are schematically illustrated, and various features and relationships between the features are shown. The FIGURE also illustrates and aids in understanding several terms used herein. Three different RNA molecules 102, 104, 106 are shown. RNA molecule 102 has a target site 110, an upstream proximal region 112, and a downstream proximal region 114. Similarly, RNA molecule 104 has a target site 120, an upstream proximal region 122, and a downstream proximal region 124. RNA molecule 106 is a small RNA that has a target site 130.

Oligodeoxynucleotides 113, 115, 117, 123, and 125 are illustrated. Oligodeoxynucleotide 113 has a sequence complementary to a RNA cleavage site 111 in the upstream proximal region 112 of the RNA molecule 102. Similarly, Oligodeoxynucleotide 115 has a sequence complementary to a RNA cleavage site 116 in the downstream proximal region 114 of the RNA molecule 102. oligodeoxynucleotide 123 has a sequence complementary to a RNA cleavage site 121 in the upstream proximal region 122 of the RNA molecule 104. Oligodeoxynucleotide 125 has a sequence complementary to a RNA cleavage site 126 in the downstream proximal region 124 of the RNA molecule 104. Oligodeoxynucleotide 117 has a sequence complementary to an RNA cleavage site 118 that is not proximal to target site 110; in other words the RNA cleavage site 118 is not in upstream proximal region 112 or downstream proximal region 114.

Target sites 110, 120, 130 represent sequences that will be analyzed in a hybridization assay, for example in a microarray assay in which the microarray has probe molecules that are complementary to the target sites. Thus, the sequence of a target site typically is known or predetermined (i.e. prior to the digestion reaction as described herein). A target site typically is at least 12 bases long, e.g. at least 15, 20 or 25 bases long. A target site is typically fewer than 100 bases long, more typically less than 60 bases long, e.g. less than 50, 40, 35, or 30 bases long. However, in certain embodiments, a target site may be shorter than 12 bases (e.g. 8, 9, 10 or 11 bases long) or longer than 100 bases (e.g. up to 125, 150, or 200 bases, or even longer).

The upstream proximal region 112, 122 is the region immediately upstream and adjacent the target site 110, 120. Similarly, the downstream proximal region 114, 124 is the region immediately downstream and adjacent the target site 110, 120. In various embodiments, the upstream and downstream proximal regions are each at least 12 bases long, e.g. at least 15, 20 or 25 bases long. In various embodiments, the upstream and downstream proximal regions each may be up to about 30 bases long, or longer, e.g. up to 40, 50, 100, 150, 200, or 250 bases long.

A DNA/RNA duplex is formed when an Oligodeoxynucleotide binds to the complementary sequence of a RNA molecule, e.g. at a RNA cleavage site. In the FIGURE, for example, when Oligodeoxynucleotide 113 binds to the complementary sequence of the RNA cleavage site 111 in the upstream proximal region 112, a DNA/RNA duplex 109 is formed. A method in accordance with the present invention results in the RNA molecule being cleaved at the site of the DNA/RNA duplex.

A RNA cleavage site is a site that is complementary to an Oligodeoxynucleotide (and is thus cleaved upon formation of a DNA/RNA duplex followed by contact with an enzyme having a DNA:RNA nuclease activity). A "target flanking site" is a RNA cleavage site located in an upstream proximal region or a downstream proximal region, for example RNA cleavage sites 111, 116, 121, 126. "A nonflanking site" is a RNA cleavage site not located in an upstream proximal region or a downstream proximal region, for example RNA cleavage site 118.

When used in the context of describing a target site, a target flanking site, an upstream proximal region, a downstream proximal region, or a RNA cleavage site, 'respective' indicates that the sequences are part of the same RNA molecule and are part of the portion of RNA molecule that includes the target sequence, the upstream proximal region adjacent that target sequence, and the downstream proximal region adjacent that target sequence. For example, the 'respective target site' of a target flanking site is the target site that is part of the same RNA molecule as that target flanking site and is adjacent to that target flanking site. Similarly, the 'respective target flanking site' of a target site is the target flanking site that is part of the same RNA molecule as that target site and is adjacent to that target site. Note that a target site typically has a respective upstream flanking site and a respective downstream flanking site. In certain embodiments some target sites may have only one respective target flanking site or may not have any respective target flanking site. An example of the latter is shown in the FIGURE as RNA molecule 106, which has a target site 130 but no target flanking site. An example of the former is an RNA molecule that has a target site at the 3' (or 5') end of that RNA molecule, and thus has only a single target flanking site. Thus, in the FIGURE, target site 110, upstream proximal region 112, downstream proximal region 114, RNA cleavage site 111, and RNA cleavage site 116 are all part of the same RNA molecule 102 and are described as being 'respective' to each other.

The FIGURE illustrates a separate strategy for digesting an RNA sample using a set of relatively short (e.g. 6-14 bases long, e.g. 8-12 bases long) oligodeoxynucleotides. The oligodeoxynucleotide 117 is directed to an RNA cleavage site that is relatively common in the long RNAs 102, 104 of the sample, based on the relatively short sequence. The arrows 140 point to sites that are complementary to member Oligodeoxynucleotides, wherein the member Oligodeoxynucleotides are 6-14 bases long, and wherein the set of Oligodeoxynucleotides has about 5 to about 200 different member Oligodeoxynucleotides. The result of digesting the RNAs in the sample in such embodiments provides RNA having a reduced average length compared to the sample of RNA. The digested RNA sample has a more uniform size distribution (compared to undigested sample). The digested RNAs (the "RNA fragments") may reduce spurious results/noise in the assay due to cross hybridization among much longer RNA molecules in the undigested sample.

Accordingly, in certain embodiments of the present invention, a method is provided as follows: A set of Oligodeoxynucleotides is obtained, the set of Oligodeoxynucleotides comprising member Oligodeoxynucleotides. Each member Oligodeoxynucleotide is directed to a RNA cleavage site in an upstream or downstream proximal region from a target site. The sample of RNA is contacted with the set of Oligodeoxynucleotides under stringent assay conditions to provide DNA/RNA duplexes, and the DNA/RNA duplexes are contacted with an enzyme having a DNA:RNA nuclease activity to provide a digested RNA sample. The digested RNA sample includes a set of RNA fragments, the set comprising member RNA fragments, each member RNA fragment having a target site, wherein each of the member RNA fragments is less than about 500 bases long.

As shown in the FIG. 1, a sample of RNA may include various RNA molecules (e.g. 102, 104, 106), including RNA molecules 102, 104 that have one or more sequences complementary to the member Oligodeoxynucleotides 114 and RNA molecules 106 that lack any sequences complementary to the member Oligodeoxynucleotides. In certain embodiments, the sample of RNA comprises small RNAs, for example miRNAs 106. Sequences that are complementary to member Oligodeoxynucleotides are indicated at features 111, 116, 118, 121, 126 (RNA cleavage sites). The set of Oligodeoxynucleotides includes one or more member oligodeoxynucleotides 113, 115, 117, 123, 125, each of the one or more member oligodeoxynucleotides 113, 115, 117, 123, 125 comprising a sequence complementary to a corresponding RNA cleavage site 111, 116, 118, 121, 126.

The RNA sample is contacted with a set of Oligodeoxynucleotides under conditions sufficient for the member Oligodeoxynucleotides 113, 115, 117, 123, 125 to hybridize to the corresponding RNA cleavage site 111, 116, 118, 121, 126 to provide DNA/RNA duplexes (e.g. 109). The DNA/RNA duplexes 128 are then contacted with an enzyme having a DNA:RNA nuclease activity to result in cleavage of the RNA, thereby providing a digested RNA sample.

Conditions under which the sample of RNA is contacted with the set of Oligodeoxynucleotides typically are selected to favor DNA/RNA duplex formation over RNA/RNA duplex formation (e.g. resulting from RNA molecules in the sample of RNA binding to the sequences that are complementary to other RNA molecules in the sample of RNA, or intramolecular binding of sequences in the same RNA molecule which are complementary to each other). Such conditions typically may be provided by adjusting the concentration of the set of Oligodeoxynucleotides to be in molar excess over any competing RNAs present in the sample when the sample of RNA is contacted with the set of Oligodeoxynucleotides. Appropriate concentrations of the oligodeoxynucleotides in the set of Oligodeoxynucleotides may be readily determined given the disclosure herein and ordinary skill in the art, for example, by running a group of dilution experiments to determine what concentration of the components provides acceptable results. In certain embodiments, selection of member oligodeoxynucleotides may be based on experimental observation of binding to and subsequent cleavage of RNA molecules in a sample of RNA. The temperature and buffer composition are selected to provide for stable DNA/RNA duplex formation between the oligodeoxynucleotides and the corresponding RNA cleavage sites in the sample of RNA. Stringent hybridization conditions are typically employed.

In typical embodiments, the DNA/RNA duplexes are contacted with an enzyme having the DNA:RNA nuclease activity to provide a digested RNA sample. This contacting is done under conditions sufficient to allow the enzyme to contact the DNA/RNA duplexes and to cleave the RNA strand of each DNA/RNA duplex to provide the digested RNA sample. Under typical conditions in exemplary embodiments, the digested RNA sample will have RNA with reduced average length compared to the sample of RNA. The digested RNA sample results in sample having more uniform size distribution (compared to undigested sample). The digested RNAs (the "RNA fragments") may reduce spurious results/noise in the assay due to cross hybridization among much longer RNA molecules in the undigested sample. Conditions for contacting the DNA/RNA duplex with the enzyme having the DNA:RNA nuclease activity are typically known in the literature or are routine and may also typically be obtained from the supplier of the enzyme having the DNA:RNA nuclease activity. After the digested RNA sample is obtained, it may be analysed by any known method for analyzing samples containing RNA.

The enzyme having the DNA:RNA nuclease activity may be any enzyme known to be capable of specifically cleaving at DNA/RNA duplexes. The enzyme having a DNA:RNA nuclease activity should be selected such that the enzyme is capable of digesting at least a portion of the RNA molecule at the site of the DNA/RNA duplex (i.e. the portion of the sequence of the RNA molecule that is complementary to the DNA and is bound to the DNA via base-pairing interaction). "Digesting" in this regard references a cleavage of one or more internucleotide bonds in the RNA molecule at the site of the DNA/RNA duplex. "DNA:RNA nuclease activity" refers to an activity of an endoribonuclease that specifically hydrolyzes the phosphodiester bonds of RNA which is hybridized to DNA (i.e. forming a DNA/RNA duplex), but does not digest single or double-stranded RNA. Selection of the enzyme having a DNA:RNA nuclease activity will typically be based on availability of the enzyme and activity of the enzyme under the desired reaction conditions for the formation of the DNA/RNA duplex and the digestion of the RNA at the RNA/DNA duplex by the enzyme (e.g. temperature, pH, ionic strength, source of RNA, structural feature of RNA, concentration of RNA, presence of other materials (e.g. contaminants, salt, surfactant, other solvents) etc.) In typical embodiments, the enzyme having an DNA:RNA nuclease activity does not cause substantial digestion of RNA that is not part of a DNA/RNA duplex, i.e. the nuclease activity is specific for the DNA/RNA duplex. In this regard, "substantial digestion" refers to a loss of greater than 50% of observable signal relative to a control experiment under essentially similar conditions using an enzyme that does not cause digestion of RNA that is not part of a DNA/RNA duplex.

A typical example of an enzyme having the DNA:RNA nuclease activity is RNase H, available from Pharmacia (Piscataway, N.J.). In certain embodiments, a thermostable enzyme having the DNA:RNA nuclease activity is employed, such an enzyme is HYBRIDASE thermostable RNase H, available from Epicentre (Madison, Wis.), or an RNase H obtained from *Thermus thermophilus*. See Guatelli et al., Proc. Nat. Acad. Sci. (1990) 87:1874-78; Bekkaoui et al., BioTechniques (1996) 20: 240-48. In particular embodiments, however, a non-thermostable enzyme is selected, allowing inactivation of the enzyme by a relatively simple heat treatment once the digestion of the DNA/RNA duplex is conducted. Thus, in some embodiments, a method in accordance with the present invention may include inactivating or removing the enzyme having the DNA:RNA nuclease activity after the enzyme has cleaved the DNA/RNA duplexes to provide the digested RNA sample, such as by heat inactivation or by using precipitation methods, chromatography methods, or other purification methods to effect a separation of the RNA in the RNA sample from the enzyme having the DNA:RNA nuclease activity.

RNase H is known to require as few as four paired bases in a DNA/RNA duplex to act as an endonuclease, thus the member oligodeoxynucleotides of the set of oligodeoxynucleotides should each be at least four bases long. This may of course vary depending on the specific enzyme used. In typical embodiments, an oligodeoxynucleotide will be at least about 8 bases long, or at least about 10 bases long, or at least about 12 bases long, or at least about 14 bases long. In typical embodiments, an oligodeoxynucleotide may be up to about 20 bases long, or up to about 25 bases long, or up to about 30 bases long, or even longer, such as up to about 50 bases long, or up to about 100 bases long, or more. In certain embodiments, a single oligodeoxynucleotide may include a plurality of sequences that are complementary to RNA cleavage sites (e.g. concatenated together, optionally the sequences that are complementary to RNA cleavage sites may be linked together via 'spacer' sequences), wherein each of the plurality of sequences may be complementary to the same or different RNA cleavage sites.

In usual embodiments each member oligodeoxynucleotide comprises a sequence complementary to an RNA cleavage site. The RNA cleavage site is typically at least 16 bases long, e.g. at least 18, 20, 22, or 25 bases long. In typical embodiments, the RNA cleavage site typically may be up to about 30 bases long, or up to about 40 bases long, or up to about 60 bases long, or even longer, such as up to about 100 bases long. However, in some embodiments in accordance with the present invention, a RNA cleavage site may have a size other than the values listed in this paragraph. In certain embodiments, each member Oligodeoxynucleotide typically binds to a single species of RNA (e.g. a single mRNA or other RNA species in the sample). This is because the size of the Oligodeoxynucleotides allows high specificity in binding to a particular sequence. The set of Oligodeoxynucleotides typically includes at least 50, 100, 200, 300, 400 or more different member oligodeoxynucleotides. In particular embodiments, each member oligodeoxynucleotide comprises at least one sequence complementary to a RNA cleavage site. The set of Oligodeoxynucleotides may be obtained from any available source, e.g. a commercial source, or may be synthesized chemically or isolated from a biological source. In some embodiments, the set of Oligodeoxynucleotides may have up to about 500, 600, 800, 1000, 4000, 10,000 or more different member oligodeoxynucleotides.

In an embodiment, the set of Oligodeoxynucleotides is synthesized on a solid support followed by cleaving the synthesized set of Oligodeoxynucleotides from the solid support. As an example, many different oligodeoxynucleotides may be synthesized in parallel, e.g. on a solid planar support or in a multiwell plate holding insoluble supports such as beads, where the oligodeoxynucleotides are bound to the support(s) by a cleavable linker. See, e.g., Pon, R T, et al., Nucleic Acids Res. 32:923-631 (2004). When the synthesis is complete, the cleavable linker may be cleaved to release the set of oligodeoxynucleotides into solution. The solution containing the set of oligodeoxynucleotides is then recovered and used as a source of the set of Oligodeoxynucleotides.

As mentioned herein, a member oligodeoxynucleotide may include one or more base insertions, deletions and/or substitutions relative to the RNA cleavage site (so long as the member oligodeoxynucleotide still hybridizes to the RNA cleavage site under the conditions of the hybridization reaction). In particular embodiments, the set of Oligodeoxynucleotides includes at least one member oligodeoxynucleotide comprising a sequence complementary to a RNA cleavage site, wherein the sequence includes one or more base insertions, deletions and/or substitutions relative to the RNA cleavage site.

In some embodiments each member oligodeoxynucleotide comprises a sequence complementary to an RNA cleavage site. The RNA cleavage site is typically at least 6 bases long, e.g. at least 7, 8, or 9 bases long. In typical embodiments, the RNA cleavage site typically may be up to about 10 bases long, or up to about 11 bases long, or up to about 12 bases long, or even longer, such as up to about 14 bases long. However, in some embodiments in accordance with the present invention, a RNA cleavage site may have a size other than the values listed in this paragraph. The set of Oligodeoxynucleotides typically includes at least one, two, three, four, five, or more different member oligodeoxynucleotides. In particular embodiments, each member oligodeoxynucleotide comprises at least one sequence complementary to a RNA cleavage site. The set of Oligodeoxynucleotides may be obtained from any available source, e.g. a commercial source, or may be synthesized chemically or isolated from a biological source. In some embodiments, the set of Oligodeoxynucleotides may includes up to 10, 15, 20, 25, 30, 40, 50, 100, or 200 different member oligodeoxynucleotides.

In particular embodiments, the member oligodeoxynucleotides of the set of Oligodeoxynucleotides are selected such that the DNA/RNA duplexes formed will have similar thermal stabilities (compared to each other). The melting temperature ('$T_m$') of the DNA/RNA duplexes should be high enough to eliminate or reduce any non-specific binding (e.g. preventing non-complementary sequences from forming double-stranded structures). In such embodiments, the melting temperatures of at least 80% of the DNA/RNA duplexes will be within about 15° C. of each other, typically within about 12° C. of each other, about 10° C. of each other, or about 5° C. of each other. In such embodiments, the DNA/RNA duplexes have a melting temperature in a range of about 15° C., within about 11° C., or within about 5° C. of each other. In certain embodiments, the difference between the maximum and minimum melting temperatures is less than about 20° C., less than about 15° C., less than about 10° C., or less than about 5° C. In some embodiments, oligodeoxynucleotide sequences may be selected based on experimental determinations of their melting temperatures or calculations of their theoretical melting temperatures; or putative oligodeoxynucleotide sequences may first be selected based on calculations of their theoretical melting temperatures and then be confirmed experimentally. Methods for determining the melting temperature of nucleic acid duplexes are known in the art. See for example, Sambrook and Russell (2001) Molecular Cloning: A Laboratory Handbook, 10.38-10.41 and 10.47, which is incorporated by reference in its entirety.

A value for melting temperature can be determined mathematically using equations and algorithms known in the art. For duplex oligonucleotides shorter than 25 bp, "The Wallace Rule" can be used in which:

$T_m$ (in ° C.)=2(A+T)+4(C+G), where (A+T)—the sum of the A and T residues in the oligonucleotide, (C+G)—the sum of G and C residues in the oligonucleotide (see Wallace et al., Nucleic Acids Res. (1979) δ: 3543-3557). Computer programs for estimating $T_m$ are also available (see, e.g., Le Novere, Bioinformatics (2001) 17(12): 1226-1227). VisualOmp (DNA Software, Inc., Ann Arbor, Mich.) is an example of commercially available software for calculating nucleic acid duplex melting temperature.

A method in accordance with the present invention may further include contacting the digested RNA sample with an enzyme having a DNA nuclease activity to result in digestion of the set of Oligodeoxynucleotides. "DNA nuclease activity" refers to an activity of an endonuclease that nonspecifically cleaves DNA, including cleaving single stranded DNA and double stranded DNA, but does not digest single or double-stranded RNA. Selection of the enzyme having a DNA nuclease activity will typically be based on availability of the enzyme and activity of the enzyme under the desired reaction conditions for the digestion of the DNA by the enzyme (e.g. temperature, pH, ionic strength, presence or concentration of RNA, presence of other materials (e.g. contaminants, salt, surfactant, other solvents) etc.) In typical embodiments, the enzyme having a DNA nuclease activity does not cause substantial digestion of RNA, i.e. the nuclease activity is specific for the DNA. One example of an enzyme having a DNA nuclease activity is DNase I, available from Pharmacia, although other enzymes having DNA nuclease activity may be selected instead. In some embodiments, the set of Oligodeoxynucleotides may compete with the RNAs in the digested RNA sample for binding sites that are complementary during further analysis, e.g. by hybridization. Digestion of the set of Oligodeoxynucleotides reduces the competition, enabling a more sensitive assay for the RNAs in the digested RNA sample. Conditions employed for contacting the digested RNA sample with an enzyme having a DNA nuclease activity are typically known in the art, and need not be further detailed here. Other experimental parameters may be selected based on known ranges for the experimental parameters or determined through routine experimentation based on, e.g. efficacy of the digestion reaction. Such other experimental parameters may include, e.g. temperature, pH, ionic strength, source of RNA and/or enzyme, structural feature of RNA, concentration of RNA, concentration of DNA, presence of other materials (e.g. contaminants, salt, surfactant, other solvents) etc.

The sample of RNA may be obtained from any source. For example, the sample of RNA may be any RNA sample, typically a sample containing RNA that has been isolated from a biological source, e.g. any plant, animal, yeast, bacterial, or viral source, or a nonbiological source, e.g. chemically synthesized. Samples of RNA may be obtained from sources reflecting different developmental stages, tissue samples, disease states, as well as any individual and/or abnormal variations. In particular embodiments, the sample includes isolated RNA that includes RNA species representing a wide range of sizes of RNA, e.g. the sample results from an isolation protocol for RNA that provides a 'whole RNA' fraction. A whole RNA fraction includes RNA species such as ribosomal RNAs, messenger RNAs, small RNAs, and other RNAs representative of a substantial portion of RNAs found in a biological source. (In this regard "substantial portion" typically indicates at least 5%, e.g. at least 10%, 20%, 30%: 40%, 50%, or more, and up to 90% or more, e.g. 95% or more, where the percentage is calculated as the {(mass of RNA in the sample)/(mass of RNA estimated in the biological source from which the RNA was isolated)}×100%.) As such, a whole RNA fraction includes RNA species having sizes ranging from about 10 bases up to about 10,000 bases, or even more.

In particular embodiments, the sample of RNA includes one or more short RNAs, such as e.g. short interfering RNAs (siRNAs), microRNAs (miRNA), tiny non-coding RhTAs (tncRNA) and small modulatory RNA (smRNA). See Novina et al., Nature (2004) 430:161-164. In certain embodiments, the small RNA targets may include isolated miRNAs, such as those described in the literature and in the public database accessible via the website located by placing "www" in front of ".sanger.ac.uk/cgi-bin/Rfam/mirna/browse.pl". In particular embodiments, the sample includes isolated small RNAs, e.g. the sample results from an isolation protocol for small RNA, especially RNAs less than about 500 bases long, e.g. less than about 400 bases long, less than about 300 bases long, less than about 200 bases long, less than about 100 bases long, or less than about 50 bases long. In some embodiments, the sample of RNA may be a whole RNA fraction isolated from a biological source and includes messenger RNA and small RNA. Such samples including a diverse set of RNAs, such as a whole RNA fraction, may be referenced herein as "complex" RNA samples.

In certain embodiments, the invention may further include providing an observable label that may be observed to obtain information relating to the sample of RNA, such as the presence of particular sequences of RNA present in the sample. The observable label may be any observable label known in the art, e.g. a chromophore, a fluorescent label, a spin label, a radioisotope label, a mass label, a sequence label, a chemically reactive tag, an affinity label, or any other known label. In particular embodiments, the observable label is a fluorophore selected from the group consisting of Gy3, Gy5, and an Alexa dye. Further examples of observable labels include any commercially available fluorophores that can be conjugated to mononucleotides or polynucleotides, e.g. dyes from Molecular Probes (Eugene, Oreg. and Leiden, The Netherlands) such as the Alexa Fluor series (example: Alexa 350, Alexa 430, Alexa 532, Alexa 546, Alexa 568, and Alexa 594) and the series of BODIPY conjugates. Other examples include: Tamra, Fluorescein, carboxyfluorescene, rhodamine, carboxyrhodamine, GY series, Oyster series, 6-carboxy-2',4',7',4,7-hexachlorofluorescein (HEX), 6-carboxy-4', 5'-dichloro-2', 7'-dimethoxyfluorescein (JOE or J), N,N,N', N'-tetramethyl-6-carboxyrhodamine (TAMRA or T), and 6-carboxy-X-rhodamine (ROX or R). More information about commercially available dyes for oligonucleotide conjugation can be found at the website located by placing "www" in front of ".synthegen.com". Any such dyes may potentially be used in accordance with the methods described herein. Such labels typically are well known in the art.

In particular embodiments, the RNA in the sample may already be labeled when the sample is obtained, e.g. the sample may be isolated from an organism grown in a radiolabeled medium. In an embodiment, the sample of RNA comprises RNA that has an observable label attached thereto, and this labeled sample of RNA is then contacted with a set of Oligodeoxynucleotides to provide a DNA/RNA duplex. In particular embodiments, the RNA may be labeled by following a known labeling protocol. In some such embodiments, before the sample of RNA is contacted with the set of Oligodeoxynucleotides, the sample of RNA is subjected to a labeling treatment that results in the RNA in the sample of RNA being labeled with an observable label. A particularly contemplated labeling protocol is described in copending application Ser. No. 11/048,255 entitled "RNA Labeling Method" and filed by Wang on Jan. 31, 2005. In an embodiment, the digested RNA sample is labeled with an observable label after the RNA sample has been contacted with the enzyme having the DNA:RNA nuclease activity.

In certain embodiments, after the sample of RNA is contacted with the enzyme having a DNA:RNA nuclease activity to provide a digested RNA sample, the digested RNA sample is subjected to an isolation protocol for small RNA, especially RNAs less than about 500 bases long, e.g. less than about 400 bases long, less than about 300 bases long, less than about 200 bases long, less than about 100 bases long, or less than about 50 bases long. The isolation protocol can be any fractionation method adapted to separate the RNA in the digested RNA sample based on molecular size of the RNA. Typical methods of fractionating mixtures of polynucleotides according to size are known and need not be described in detail here. This isolation step is particularly useful in embodiments in which the set of Oligodeoxynucleotides is designed to cut target sites from much longer RNAs, potentially effecting a separation of relatively short RNA fragments having the target sites from the longer 'tails' of the initially much longer RNAs. For example, if an exemplary RNA (e.g. one that looks like 102 in FIG. 1) in a sample of RNA has a single target site that is about 5% of the total length of said exemplary RNA and that is located somewhere near the middle of said exemplary RNA, then cutting the exemplary RNA typically will result in two larger fragments of about 40%-50 percent total length of said exemplary RNA, plus the ~5% fragment that contains the target site. Separating the shorter fragments in the digested sample from the longer fragments may result in increased sensitivity, increased signal to noise ratio, or otherwise have a desirable effect.

Depending on the application, the presence of the observable label in the set of Oligodeoxynucleotides may interfere with the analysis of the sample of RNA; therefore, in certain embodiments the set of Oligodeoxynucleotides lacks the observable label. In certain embodiments, the digested RNA may undergo a purification step to separate the digested RNA from the set of Oligodeoxynucleotides. Some such embodiments may involve the use of a DNAse to digest member Oligodeoxynucleotides.

In certain other embodiments, member Oligodeoxynucleotides of the set of OLIGODEOXYNUCLEOTIDES may be labeled with an observable label (possibly, though not necessarily, the same observable label used to label the RNA). In certain embodiments, the set of OLIGODEOXYNUCLEOTIDES may be labeled (i.e. the members of the set of Oligodeoxynucleotides, e.g. the oligodeoxynucleotides, may be labeled) with a first observable label, such as Cy3, and the RNA sample may be labeled with a second observable label, such as Cy5, to give distinguishable signals upon observation of the labels. Such choice of first and second labels is referred to herein as "distinguishable" labels in that the labels that can be independently detected and measured, even when the labels are mixed. In other words, the amounts of label present (e.g., the amount of fluorescence) for each of the labels are separately determinable, even when the labels are co-located (e.g., in the same tube, in the same duplex molecule, or on the same array feature). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY VI 005 (Molecular Probes, Eugene, Oreg.), POPO-3 and TOTO-3 (Molecular Probes, Eugene, Oreg.), fluorescein and Texas red (Dupont, Boston, Mass.) and POPRO3 and TOPRO3 (Molecular Probes, Eugene, Oreg.). Further suitable distinguishable detectable labels may be described in Kricka et al. (Ann Clin Biochem. 39:114-29, 2002).

In some embodiments, only one observable label moiety is attached to a labeled polynucleotide (e.g. labeled RNA molecule or labeled DNA molecule). In such embodiments, the labeled polynucleotide will consist essentially of the polynucleotide labeled with a single label moiety (i.e. each labeled polynucleotide molecule will have only one observable label moiety attached—referenced herein as a "singly-labeled" polynucleotide). This potentially provides increased ease of use in quantitative methods using the labeled polynucleotide.

In other embodiments, a labeled polynucleotide (e.g. labeled RNA molecule or labeled oligodeoxynucleotide molecule) may have a plurality of observable label moieties. Thus, the labeled polynucleotide will consist essentially of the polynucleotide labeled with a plurality of label moieties. This increased labeling of the polynucleotide may provide for greater sensitivity in analyses using the labeled polynucleotide.

In certain embodiments, methods of performing an array analysis are provided. In certain embodiments, the invention provides a method of performing an array analysis wherein the method includes labeling the RNA in the digested RNA sample to provide a labeled RNA sample. The labeled RNA sample is then contacted with an array under conditions sufficient to provide for specific binding of labeled RNA to the array. The array typically is then interrogated to provide data on binding of the labeled RNA to the array. The array typically comprises capture agents immobilized onto an array substrate, wherein the capture agents are directed to target sites of RNA present in the digested RNA sample.

Standard hybridization techniques (using stringent hybridization conditions) are used to hybridize a labeled sample to a nucleic acid array. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol 7, pgs 43-65 (Plenum Press, New York 1985). See also U.S. Pat. Nos. 6,335,167; 6,197,501; 5,830,645; and 5,665,549; the disclosures of which are herein incorporated by reference. Hybridizing the labeled sample to the array is typically performed under stringent hybridization conditions, as described herein and as known in the art. Selection of appropriate conditions, including temperature, salt concentration, polynucleotide concentration, time (duration) of hybridization, stringency of washing conditions, and the like will depend on experimental design, including source of sample, identity of capture agents, degree of complementarity expected, etc., and are within routine experimentation for those of ordinary skill in the art to which the invention applies.

Following hybridization, the array-surface bound polynucleotides are typically washed to remove unbound and not tightly bound labeled nucleic acids. Washing may be performed using any convenient washing protocol, where the washing conditions are typically stringent, as described above.

Following hybridization and washing, as described above, the hybridization of the labeled RNA sample to the capture agents is then detected using standard techniques of reading the array, i.e. the array is interrogated. Reading the resultant hybridized array may be accomplished by illuminating the array and reading the location and intensity of resulting fluorescence at each feature of the array to detect any binding complexes on the surface of the array. For example, a scanner may be used for this purpose, which is similar to the AGILENT MICROARRAY SCANNER available from Agilent Technologies, Palo Alto, Calif. Other suitable devices and methods are described in U.S. patent applications: Ser. No. 09/846,125 "Reading Multi-Featured Arrays" by Dorsel et al.; and U.S. Pat. No. 6,406,849. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, results from interrogating the array are used to assess the level of binding of the labeled RNA in the sample to capture agents on the array. The term "level of binding" means any assessment of binding (e.g. a quantitative or qualitative, relative or absolute assessment) usually done, as is known in the art, by detecting signal (i.e., pixel brightness) from a label associated with the sample, e.g. the digested sample is labeled. The level of binding of labeled RNA to capture agent is typically obtained by measuring the surface density of the bound label (or of a signal resulting from the label).

Also provided by the subject invention are kits for practicing the subject methods, as described above. The subject kits include at least a set of Oligodeoxynucleotides. In certain embodiments the subject kits may also include reagents for isolating RNA from a source to provide the sample of RNA. In some embodiments the subject kits optionally also include reagents for labeling RNA, reagents for contacting the sample of RNA with the set of Oligodeoxynucleotides, enzymes for use with the subject methods such as described above, control samples, etc. The various components of the kit may be present in separate containers or certain compatible components may be precombined into a single container, as desired.

In addition to above-mentioned components, the subject kits may further include instructions for using the components of the kit to practice the subject methods, e.g. instructions for sample analysis. The instructions for practicing the subject methods are generally recorded on a suitable recording medium. For example, the instructions may be printed on a suitable material, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable material.

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs. The description herein is put forth so as to provide those of ordinary skill in the art with a complete disclosure of the methods and compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

In particular embodiments the present invention thus provides methods of treating a sample of RNA to provide a digested RNA sample having a more uniform size distribution of smaller RNAs as compared to the undigested sample of RNA. It is expected that the present invention may provide an assay system that permits concurrent analysis of sequences (e.g. sequences at target sites) that are present in different classes of RNA, e.g. RNAs that are long (e.g. >1000 bases) and short (e.g. less than 200 bases). Such samples of RNA may be obtained from sources reflecting different developmental stages, tissue samples, disease states, as well as any individual and/or abnormal variations.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A method of sample analysis comprising:
   a) obtaining a set of oligodeoxynucleotides, the set of oligodeoxynucleotides comprising member oligodeoxynucleotides, each member oligodeoxynucleotide directed to a redundant RNA cleavage site, wherein said redundant RNA cleavage site occurs in at least two different positions in the RNA molecules in said sample;
   b) contacting the sample of RNA with a solution comprising the set of oligodeoxynucleotides under stringent assay conditions to provide DNA/RNA duplexes,
   c) contacting the DNA/RNA duplexes with an enzyme having a DNA:RNA nuclease activity to provide a digested RNA sample;
   d) labeling the digested RNA with an observable label to provide labeled RNA;
   e) contacting the labeled RNA with an array under conditions that provide for specific binding of the labeled RNA to the array; and
   f) interrogating the array to provide data on binding of the labeled RNA to the array.

2. The method of claim 1 wherein the digested RNA sample includes a set of RNA fragments, the set comprising member RNA fragments, each member RNA fragment having a target site, wherein the average length of the member RNA fragments is less than about 500 bases long.

3. The method of claim 2 wherein the average length of the member RNA fragments is less than about 300 bases long.

4. The method of claim 2 wherein each of the member RNA fragments is less than about 150 bases long.

5. The method of claim 1 wherein the redundant RNA cleavage sites are from 6 to 14 bases long.

6. The method of claim 1 wherein the redundant RNA cleavage sites are from 8 to 12 bases long.

7. The method of claim 1 wherein the sample of RNA is a whole RNA sample.

8. The method of claim 1, further comprising fractionating the digested RNA sample based on size, recovering a fraction that includes isolated RNA fragments, said fragments shorter than about 500 bases long.

9. The method of claim 8, further comprising performing an array analysis on the fraction that includes isolated RNA fragments.

10. The method of claim 1 wherein the set of oligodeoxynucleotides includes from 5 to 50 member oligodeoxynucleotides.

11. The method of claim 1, wherein each of the DNA/RNA duplexes is at least 6 bases long and is up to about 14 bases long.

12. The method of claim 1, wherein each of the DNA/RNA duplexes is at least about 8 bases long and is up to about 12 bases long.

13. The method of claim 1, further comprising:
   contacting the digested RNA sample with an enzyme having a DNA nuclease activity to result in digestion of the member oligodeoxynucleotides.

14. The method of claim 13, wherein said enzyme having the DNA nuclease activity is DNase I.

15. The method of claim 1, further comprising inactivating the enzyme having the DNA:RNA nuclease activity after the digested RNA sample is provided.

16. The method of claim 1, further comprising separating the enzyme having the DNA:RNA nuclease activity from the digested RNA sample.

17. The method of claim 1, wherein the enzyme having the DNA:RNA nuclease activity is RNase H.

18. The method of claim 1, wherein the enzyme having the DNA:RNA nuclease activity is a thermostable RNase H.

19. A method comprising:
   a) contacting a sample of RNA with a solution comprising a set of oligodeoxynucleotides under stringent hybridization conditions to provide DNA/RNA duplexes, wherein said set of oligodeoxynucleotides comprises:
      a first oligodeoxynucleotide that binds upstream of a target site and/or a second oligodeoxynucleotide that binds downstream of said target site;
   b) contacting the DNA/RNA duplexes with an enzyme having a DNA:RNA nuclease activity to provide a digested RNA sample that comprises an RNA fragment comprising said target site;
   c) labeling the digested RNA with an observable label to provide labeled RNA;
   d) contacting the labeled RNA with an array under conditions sufficient to provide for specific binding of the labeled RNA to the array; and e) interrogating the array to provide data on binding of the labeled RNA to the array.

20. The method of claim 19, wherein the digested RNA sample comprises a set of RNA fragments in which each RNA fragment comprises a target site and is less than about 500 bases long.

21. The method of claim 19, wherein at least one of said oligodeoxynucleotides is directed to a RNA cleavage site in an upstream proximal region from said target site and at least one of said oligodeoxynucleotides is directed to a RNA cleavage site in a downstream proximal region from said target site.

* * * * *

UNITED STATES PATENT AND TRADEMARK OFFICE
CERTIFICATE OF CORRECTION

| | |
|---|---|
| PATENT NO. | : 7,645,578 B2 |
| APPLICATION NO. | : 11/591260 |
| DATED | : January 12, 2010 |
| INVENTOR(S) | : Hui Wang |

It is certified that error appears in the above-identified patent and that said Letters Patent is hereby corrected as shown below:

On the face page, in field (56), under "Other Publications", in column 2, line 1, delete "nuceotides." and insert -- nucleotides. --, therefor.

In column 22, line 59, in Claim 19, delete "b)contacting" and insert -- b) contacting --, therefor.

Signed and Sealed this

Twenty-seventh Day of April, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 43
<212> TYPE: RNA

-continued

```
<213> ORGANISM: artificial sequence
<220> FEATURE:
<223> OTHER INFORMATION: exemplary (imaginary/fictional/no 'real-world'
      source) sequence for identity/similarity examples

<400> SEQUENCE: 1
uauccuccag uaacauguaa ugacgaaugg agggucuucu aau                      43

<210> SEQ ID NO 2
<211> LENGTH: 40
<212> TYPE: RNA
<213> ORGANISM: artificial sequence
<220> FEATURE:
<223> OTHER INFORMATION: exemplary (imaginary/fictional/no 'real-world'
      source) sequence for identity/similarity examples

<400> SEQUENCE: 2
auaaggucau uguauuacug cuuacgaccc aguauaguua                          40
```